United States Patent [19]

Lee

[11] Patent Number: 5,145,063
[45] Date of Patent: Sep. 8, 1992

[54] SHARPS CONTAINER

[75] Inventor: Angelene M. Lee, Missouri City, Tex.

[73] Assignee: The United States of America as represented by the Administrator of the National Aeronautics and Space Administration, Washington, D.C.

[21] Appl. No.: 772,763

[22] Filed: Oct. 7, 1991

[51] Int. Cl.⁵ .............................................. B65D 83/10
[52] U.S. Cl. .................................. 206/364; 206/366; 206/370; 206/818; 220/908
[58] Field of Search ............... 206/363, 364, 365, 366, 206/370, 438, 818; 220/315, 908

[56] References Cited

U.S. PATENT DOCUMENTS

| | | | |
|---|---|---|---|
| 3,483,494 | 12/1969 | Cromie | 206/818 |
| 3,749,274 | 7/1973 | Mele et al. | 220/908 |
| 4,032,037 | 6/1977 | Dubery et al. | 220/908 |
| 4,318,473 | 3/1982 | Sandel | 206/370 |
| 4,351,434 | 9/1982 | Elisha | 206/366 |
| 4,453,648 | 6/1964 | Harris et al. | 220/324 |
| 4,466,538 | 8/1984 | Gianni | 206/366 |
| 4,488,643 | 12/1984 | Pepper | 206/366 |
| 4,494,657 | 1/1985 | Oldenkamp | 220/908 |
| 4,558,796 | 12/1985 | Jaicks | 220/908 |
| 4,580,688 | 4/1986 | Harris et al. | 220/1 T |
| 4,596,329 | 6/1986 | Eldridge, Jr. | 206/818 |
| 4,666,054 | 5/1987 | Jaicks | 220/908 |
| 4,679,700 | 7/1987 | Tharrington et al. | 220/908 |
| 4,714,168 | 12/1987 | Johnson et al. | 220/908 |
| 4,715,498 | 12/1987 | Hanifl | 206/366 |
| 4,802,579 | 2/1989 | Hall et al. | 220/908 |
| 4,838,426 | 6/1989 | Dalbo | 206/818 |
| 4,842,138 | 6/1989 | Sandel et al. | 206/370 |
| 4,890,733 | 1/1990 | Anderson | 206/365 |
| 4,928,823 | 5/1990 | Campbell | 206/818 |
| 4,940,250 | 7/1990 | Corrado | 206/818 |
| 4,955,477 | 9/1990 | Bruno | 220/908 |
| 5,046,614 | 9/1991 | Torres et al. | 220/908 |

Primary Examiner—David T. Fidei
Attorney, Agent, or Firm—Russell E. Schlorff; Guy M. Miller; Edward K. Fein

[57] ABSTRACT

A Sharps container constructed from lightweight alodined non-magnetic metal material with a cup member having an elongated tapered shape and a length greater than its transverse dimensions. A magnet in the cup member provides for metal retention in the container. A non-magnetic lid member has an opening and spring biased closure flap member. The flap member is constructed from stainless steel. A Velcro patch on the container permits selective attachment at desired locations.

4 Claims, 1 Drawing Sheet

SHARPS CONTAINER

ORIGIN OF THE INVENTION

The invention described herein was made by an employee of the United States Government and may be manufactured and used by or for the Government of the United States of America for governmental purposes without the payment of any royalties thereon or therefor.

FIELD OF THE INVENTION

This invention relates to a system for use in disposing of potentially hazardous items and more particularly a sharps receptacle for used hypodermic needles and the like.

BACKGROUND OF THE INVENTION

Sharps containers for used hypodermic needles are well known. It is normal practice in hospitals, for example, to provide disposal boxes to receive different types of medical refuse for disposal. One special class of items for disposal is commonly referred to as "Sharps" and includes items such as used hypodermic needles, or broken glass phials or pharmaceutical containers. After use these articles may be potentially very dangerous, if not unsanitary or unhygenic. Some of the articles may, for example, be coated with blood or contaminated in other ways. Other objects may still carry quantities of drugs and in addition there is the physical danger of injury to hands or fingers from the presence of sharp points or edges. Attempts have been made to provide disposal containers for such items but existing containers for the purpose suffer from various disadvantages and it is an object of this present invention to provide an improved container which will meet some of the requirements and satisfy some of the present problems.

Commercially available sharps containers used in hospitals and laboratories to guard against accidental use of used needles typically utilize devices which cause the needle to be broken off at the end of a syringe or act as a receptacle for the needle assembly or sometimes a receptacle for both the needle and syringe. Currently available Sharps containers are gravity dependent in that the disposed item is dropped or inserted into the container and falls to the bottom of the container. In a space environment and the absence of gravity there are some problems in introducing and retaining a disposable item in presently available Sharps containers. Plastic containers also present an off-gassing and flammability problem.

Some representative off the shelf Sharps containers include the following.

1. The Becton Dickinson "Destruclip One" which is basically a plastic box with a cutting mechanism in the lid. The waste container and lid are made of homopolymer polypropylene and are autoclavable. The cutting mechanism works through a hinged blade that is connected to one of the clipping handles. After the handles have been squeezed together, a spring attached to the blade pulls the handles open and back into their original position. The plastic construction does not protect against off-gassing products. Secondly, the openings in the device must be closed in order to prevent fragments of material from exiting the container and finally the container requires gravity for the needles to fall into the container. The device also requires use of two hands, one to hold the needle assembly and the other to squeeze the cutting handles.

There are instances when it is preferable to dispose of the entire needle assembly without having to remove the needle, recap it or in any way use more than one hand to operate the sharp.

2. Other sharps containers are simply large cups with locking lids or hinged lids where the operator simply drops the needle assembly into the container through an opening in the lid that can be locked when the unit is full. These kinds of devices are gravity dependent and may not safely contain the sharps as described above.

3. Still other sharps containers have lids which have a flexible fabric or plastic cover with slits such that the sharp can pass through the slits in the lid but will not be able to back out. These lids are unsuitable because needles can pierce the cover instead of passing through. The lid cover also can be deformed in usage so that the slits lose their elasticity and will not properly close the opening. These types of containers typically also have large volumes and are gravity dependent.

PRIOR PATENT ART

U.S. Pat. No. 4,351,434 issued Sep. 28, 1982 to Benjamin Elisha relates to a container for the disposal of hypodermic needles only. A tubular container has a diameter less than the length of a needle and the top cover (which can be removed) has 4 slots at 90° and a center hole. The hub of a needle has a non-circular cross section which can locate in the hole and the slots to permit a rotative release of a needle from a syringe before pushing the needle into the container. The hole is smaller than the needle hub which also assists separation of the hub from the hypodermic body.

U.S. Pat. No. 4,453,648 issued Jun. 12, 1984 to John Harris relates to a disposable container for hypodermic needles. The container is for various disposable medical items which is a square or rectangular container constructed of plastic. The top cover is made of translucent material. In the top cover is a tapered chute which is closed by a transparent hinged door. On the internal section of the container the door has a bar with a knife edge. Needles are disposed in the container by insertion through a keyhole slot so that a needle can be inserted through the opening and separated from the hypodermic body by use of the slot. When the container is full, a probe is inserted into the keyhole opening and engages the knife edge to retain the lid in a closed condition. The access door is gravity dependent for operation.

U.S. Pat. No. 4,466,538 issued Aug. 21, 1984 to R. F. Gianni relates to a receptacle for used hypodermic needles. A disposable plastic bottle has an upper rectangular cross section connected to a lower inwardly tapered section and to an upper circular opening. The cylindrical opening is arranged to receive a lid with a triangular opening with a serrated edge for gripping a needle. A cap member with a triangular opening is rotatably mounted on the housing opening. Needles are disposable in the container through the triangular opening and fall by gravity to the bottom of the container. The cap member is rotatable to close off the container. The container is larger than the sharps object which can re-orient themselves in the container.

U.S. Pat. No. 4,488,643 issued Dec. 18, 1984 to K. V. Pepper relates to needle disposal. In the Pepper system needles can be bent and then dispatched through a one-way valve formed of resilient deformable material and fold lines which define four downwardly depending deflectable flaps in a touching relationship. A needle is insertable through the flaps which automatically close after a needle is inserted. The container and lid are formed from thermoplastic resins.

U.S. Pat. No. 4,890,733 issued Jan. 2, 1990 to R. S. Anderson relates to sharps disposal container where the cover of the container is provided with a pivotally mounted "L" shaped tray in which disposables can be placed and pivotally moved by the tray into the interior of the container by maintaining the closed integrity of the container. The device is gravity dependent for operation.

U.S. Pat. No. 4,842,138 issued Jun. 27, 1989 to D. Sandel relates to a disposable sharps container with a one-way barrier valve. Needles are insertable through an opening with a one-way flap. The device is gravity dependent.

U.S. Pat. No. 4,715,498 issued Dec. 29, 1987 to P. H. Hanifl utilizes a pivotal tray member at the entrance of a container which pivots to permit entry of sharps to the container. The device is gravity dependent.

U.S. Pat. No. 4,580,688 issued Apr. 8, 1986 to J. Harris et al. relates to a sharps container with a swinging door. The device is gravity dependent.

SUMMARY OF THE PRESENT INVENTION

The present invention is embodied in a sharps container which has a small volume, gravity independence, flight quality materials and a one way entrance. The sharps container basically consists of a lid and a waste cup which are machined out of aluminum and are alodine gold. The aluminum is a standard flight approved material and is light weight. Alodining the aluminum helps to prevent corrosion and presents no known toxic hazards due to off-gassing. After use, the unit can be emptied, cleaned and reused.

The waste cup of the container has a conical taper to a narrower bottom which allows several disposable units to be stored and the narrower diameter of the cup prevents the larger needle assemblies from moving or re-orienting their direction in the absence of gravity toward the lid. The larger needle assemblies are entered needle first and remain in a needle first positioning in the waste cup. A magnet is attached to the bottom of the waste cup to attract the needles away from the opening. A hook and loop fastener, such as a VELCRO fastener patch is attached to the outside of the waste cup so that the device can be attached to a wall or workbench or wherever the container may be needed.

The lid of the container is threaded so that it will screw on to the top of the cup. Attached to the underside of the lid is a spring hinge assembly with a flat member which performs as a one-way entry to the container. The flap member of the spring hinge assembly is constructed of 304 stainless steel since it has greater resistance to corrosion and scratching than aluminum and the impact resistance material prevents undue wear when used needles are frequently in contact with the door flap member. The hinge assembly is anchored to the lid by two screws which causes the spring in the hinge to be placed in tension. The diameter of the door flap member is greater than that of the opening of the lid and the tension in the spring keeps the flap member firmly pressed against the underside of the lid. Pressure on the door flap member from the outside of the container will force the flap member to swing into the waste cup and once the pressure is released the tension of the spring snaps the flap member shut again. Pressure from the interior only pushes the flap member more firmly against the underside of the lid.

DESCRIPTION OF THE PRESENT INVENTION

Figure 1:
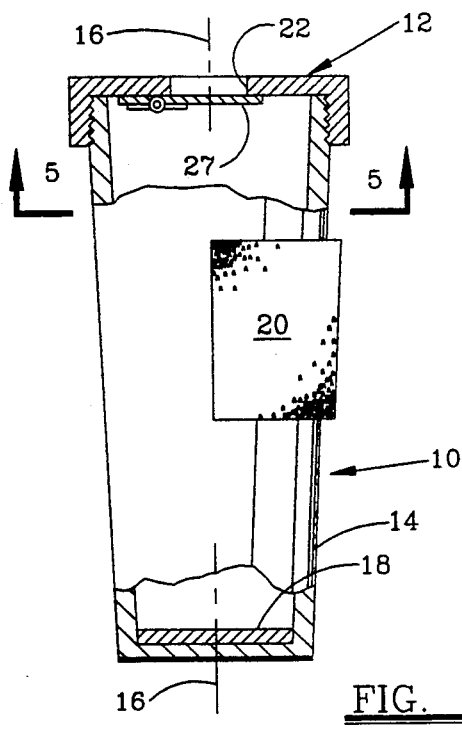
FIG. 1 is a side view in partial longitudinal cross section of a sharp container of the present invention.

In an orbiting space vehicle studies are conducted of how zero-g affects the orbiting environment and includes analysis, for example, of the formation of water droplets, growing crystals and of the human body. Some of the studies focus upon cardiovascular system, vestibular responses, lymphocyte proliferation and pulmonary function. Many of these studies require metabolic data and other information that is acquired only by taking blood samples from a crew member. To do this there is an in-flight blood collection system which consists principally of conventional off the shelf blood collection items such as syringes, needles, gauze, bandaids, glass tubes, tourniquets and catheters and is no more difficult to use in microgravity than on earth. However, some of these items, under conditions of microgravity and particularly after use, are not reused and require disposal. For example, hypodermic needle and other sharps. Sharps refers to a class of items for disposal which includes hypodermic needles, broken glass vials or pharmaceutical containers.

For crew safety it is desirable to have a sharps container which is utilitarian in a zero-g environment. In the present invention a sharps container 10 consists basically of two parts, a lid member 12 and a waste cup member 14. Both are machined out of 6061 T6 aluminum and both are alodined gold. The aluminum is a standard flight approved material and alodining helps to prevent corrosion. The metal construction presents no known toxic hazards due to off-gassing. Since the entire unit is metal, after use it can be emptied, cleaned and reused.

The waste cup member 14 has a tapered or frustoconical configuration and is elongated along a lengthwise extending axis 16. The tapered shape of the waste cup member allows several elongated devices such as hypodermic needles to be nested side by side thus allowing for easier stowage. The length of the waste cup member is preferably more than two times the narrowest diameter of the waste cup member to prevent the larger needle assemblies from randomly floating and so that the needle points cannot reverse position and point toward the lid member. A hypodermic syringe is inserted needle first and remains that way to prevent an accident in the event a finger is inserted through the opening in the lid. A cylindrically shaped disc magnet 18 is attached to the bottom of the waste cup member in any suitable manner and provides a magnetic attraction to retain the needles in their location facing away from the entrance opening. This is particularly advantageous in the case of smaller assemblies where the motion of the disposable items are not necessarily inhibited by the length and diameter of the cup. In addition, on the exterior surface of the waste cup member is a hook and loop fastening patch 20 so that the container cup member can be attached to a wall or work bench where desired, while not in use, or while being used.

Figure 2:
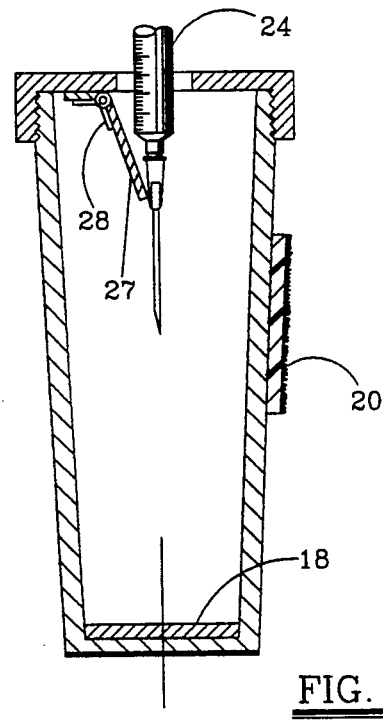
FIG. 2 is a longitudinal view in longitudinal cross section of the sharps container of the present invention showing insertion of a hypodermic needle.
Figure 3:
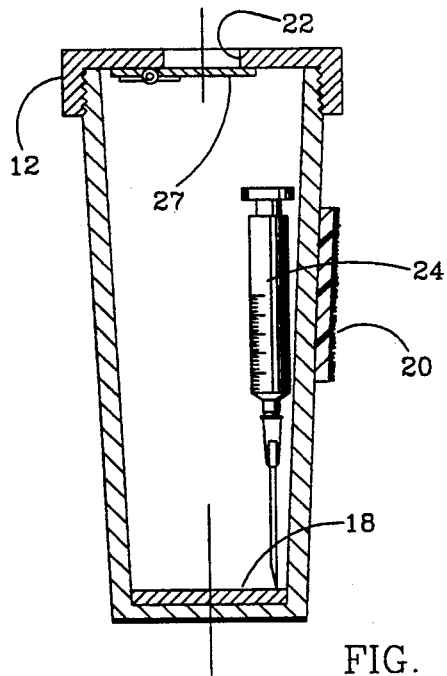
FIG. 3 is a view in longitudinal cross section of a sharps container of the present invention with a needle disposed in a sharps container.
Figure 4:
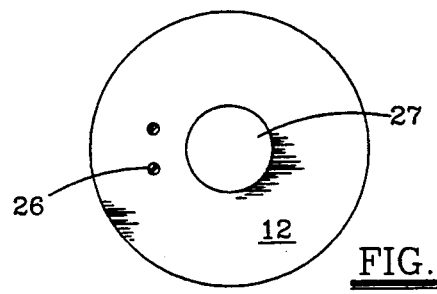
FIG. 4 is a top view of the sharps container of FIG. 1.
Figure 5:
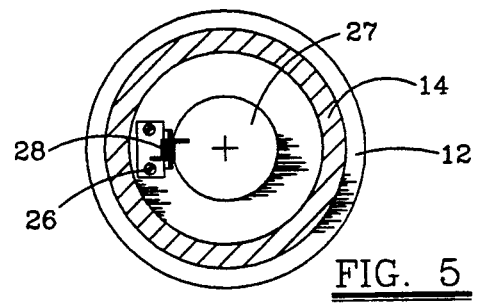
FIG. 5 is a view taken along 5—5 of FIG. 1 of the bottom side of the lid.

The lid member 12 of the container is threadedly coupled to the waste cup member. A central opening 22 in the lid member is sized to receive a disposable sharps unit 24 (see FIG. 2). Attached to the underside of the lid member is a spring hinge assembly 26 which performs as a one way entry to the waste cup member 14. The spring hinge assembly 26 has a flap member 27 which is constructed of 304 stainless steel which has greater resistance to corrosion and scratching than aluminum and which provides a stronger impact resistant surface which will not wear with repetitive use. The spring hinge assembly 26 is anchored to the lid member by screws 26 or the like which cause the spring 28 in the hinge assembly to be placed in tension. The diameter of a door flap member 27 is greater than the opening 26 in the lid member. The spring tension keeps the flap member 27 firmly pressed against the underside of the lid member. Pressure on the door flap member from the outside of the container will force the flap member to swing into the interior of the waste cup and once the pressure is released the tension of the spring snaps the flap member 27 shut again. Pressure from the interior only pushes the door flap member 27 more firmly against the underside of the lid member so as a result, objects can enter the sharps container but they cannot exit.

It will be apparent to those skilled in the art that various changes may be made in the invention without departing from the spirit and scope thereof and therefore the invention is not limited by that which is enclosed in the drawings and specifications but only as indicated in the appended claims.

I claim:

1. A sharps container for disposal of elongated hypodermic needles comprising:
    a hollow waste cup member constructed from a light weight nonmagnetic metal material and having a tapered configuration about a longitudinal axis from a larger open end to a smaller closed end,
    a lid member constructed from a light weight nonmagnetic metal material and having a threaded releasable interconnection with said open end of said cup member,
    said lid member having a central entrance opening sized to lengthwise receive an elongated hypodermic needle, said cup member having a length dimension greater than the length of the elongated hypodermic needles and said length dimension being greater than the largest transverse dimension of said cup member for preventing re-orientation of elongated hypodermic needles in said cup member after insertion into the cup member,
    said lid member having an internally located flap member constructed of impact resistance metal material,
    resilient means for biasing said flap member to a closed position on said opening thereby providing a one-way closure for said waste cup member, and
    magnetic means attached to the closed end of the cup member providing magnetic attraction to retain the hypodermic needles facing away from the entrance opening.

2. The apparatus as set forth in claim 1 wherein said cup 2 member has a hook and loop fastener mounting strip on its outer surface.

3. The apparatus as set forth in claim 1 wherein said flap 2 member is constructed from stainless steel.

4. A method for disposal of sharps in a microgravity environment comprising the steps of:
    attaching an elongated sharps container adjacent to a workstation generating used elongated hypodermic needles;
    the sharps container being formed of a tapered cup member with the large end being closed by a detachable lid member and a magnet located at the small end, the lid having an inwardly opening, biased closed valve member;
    disposing of the elongated hypodermic needles by inserting the elongated hypodermic needles endwise through the valve opening in said sharps container where said sharps container has a length greater than the largest transverse dimension of said container; and
    securing said sharps in said container by magnetically attaching said sharps to the bottom wall of said container.

* * * * *